United States Patent [19]

Tedder

[11] 4,399,000
[45] Aug. 16, 1983

[54] PROCESS FOR PRODUCING ABSOLUTE ALCOHOL BY SOLVENT EXTRACTION AND VACUUM DISTILLATION

[75] Inventor: Daniel W. Tedder, Marietta, Ga.

[73] Assignee: Georgia Tech Research Institute, Atlanta, Ga.

[21] Appl. No.: 309,258

[22] Filed: Oct. 7, 1981

[51] Int. Cl.³ .............................................. C07C 27/34
[52] U.S. Cl. ....................................... 203/19; 203/24; 203/43; 203/91; 203/DIG. 4; 203/DIG. 13; 203/18; 435/161; 435/813; 568/916; 568/918
[58] Field of Search ............... 203/24, DIG. 4, 19, 203/43, DIG. 13, 91, 18, 89, 9; 435/161, 813; 568/918, 916, 913; 202/168–170, 236; 426/494

[56] References Cited

U.S. PATENT DOCUMENTS

| | | | |
|---|---|---|---|
| 2,127,004 | 8/1938 | Nelson | 203/DIG. 4 |
| 2,182,550 | 12/1939 | Christensen | 435/160 |
| 2,440,925 | 5/1948 | Boeckeler | 203/43 |
| 2,597,009 | 5/1952 | Lobo et al. | 568/916 |
| 3,282,797 | 11/1966 | Hammer | 202/236 |
| 3,292,683 | 12/1966 | Buchi et al. | 202/236 |
| 3,351,119 | 11/1967 | Rosenblad | 202/236 |
| 4,143,066 | 3/1979 | Kalcevic | 203/43 |
| 4,161,429 | 7/1979 | Baiel et al. | 203/19 |
| 4,306,884 | 12/1981 | Roth | 203/19 |
| 4,308,106 | 12/1981 | Mannfeld | 203/24 |
| 4,309,254 | 1/1982 | Dahlstrom et al. | 203/19 |

Primary Examiner—Wilbur L. Bascomb, Jr.
Attorney, Agent, or Firm—Newton, Hopkins & Ormsby

[57] ABSTRACT

Alcohol substantially free of water is produced by a process comprising extracting an aqueous alcohol solution with an organic solvent system containing an extractant for said alcohol thereby forming an organic solvent-alcohol phase and an aqueous phase, and vacuum distilling said organic solvent-alcohol phase thereby obtaining the product alcohol substantially free of water.

13 Claims, 1 Drawing Figure

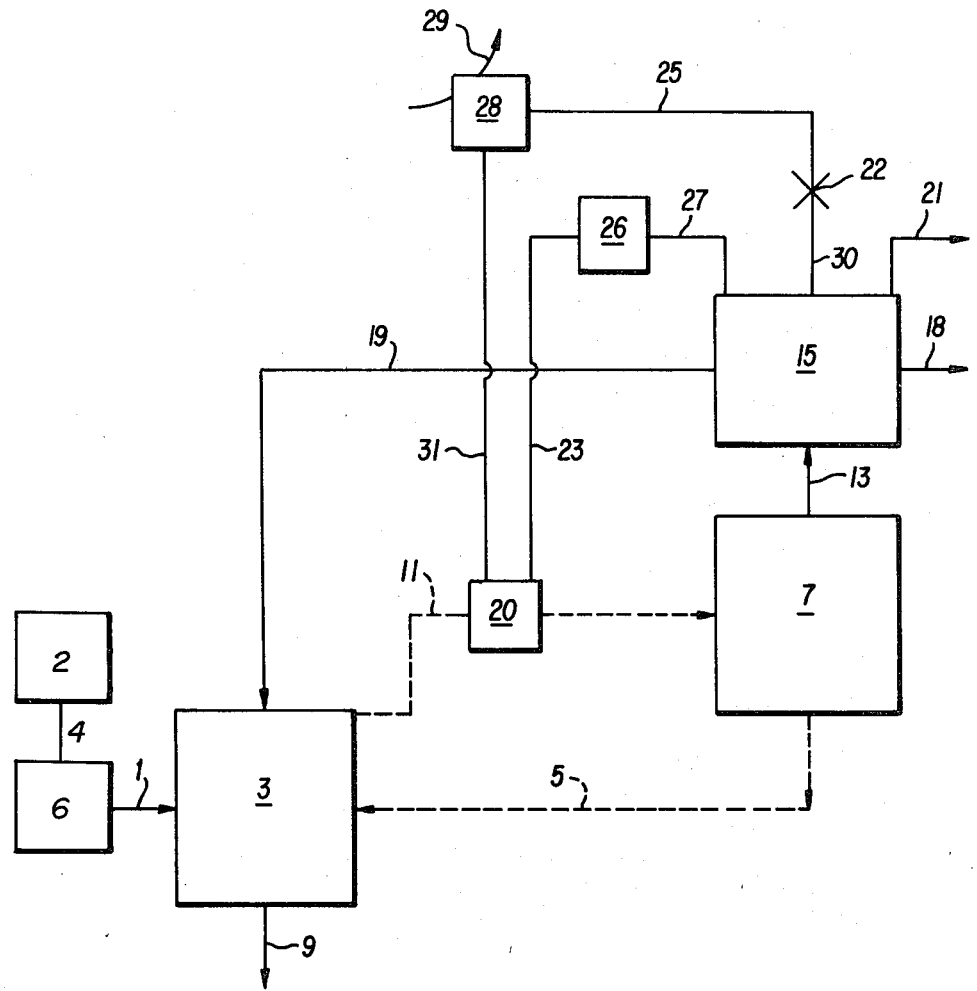

PROCESS FOR PRODUCING ABSOLUTE ALCOHOL BY SOLVENT EXTRACTION AND VACUUM DISTILLATION

BACKGROUND OF THE INVENTION

1. Field of the Invention

The present invention relates to a method for preparing absolute alcohol.

2. Description of the Prior Art

In the conventional process for recovering ethanol from fermentation liquors, the dilute liquors obtained by fermentation of a suitable fermentable liquid material are passed through a beer still in which the ethanol and water are stripped from the liquor, usually by steam stripping, and the liquors are separated from nonvolatile dissolved solids. The solid free liquid product obtained from this step is only slightly enriched in ethanol. Thereafter, the ethanol/water mixture obtained is passed into a fractionator in which distillation of the liquid mixture occurs to produce an overhead which is about a 95% ethanol azeotrope and water is withdrawn as a bottoms product. In the conversion of the 95% ethanol-water azeotrope to absolute ethanol the azeotrope is distilled with benzene or a comparable hydrocarbon which breaks-up the azeotrope.

An analysis of the conventional alcohol distillation process shows that the total amount of energy required to obtain absolute ethanol from the fermentation liquor is at least 60% of the theoretical heating value of the ethanol product. This is a significant disadvantage for the large scale production of essentially water free ethanol for use as an ingredient in the production of gasoline-alcohol mixtures (commonly known as gasahol) which are to be used as motor fuels. If, in fact, ethanol is to find acceptable commercial utility as a motor fuel ingredient, the energy required to produce the substantially water free ethanol must be less than the energy that can be recovered from the combustion of the ethanol as a fuel. Moreover, the conventional distillation and recovery process is complicated since it requires three distinct processing steps which are the (1) beer still, (2) the fractionator and (3) the azeotropic distillation of the alcohol-water mixture with benzene or other similar drying agent. A need, therefore, continues to exist for a method by which substantially water free alcohol can be obtained using significantly less energy for the recovery of ethanol in comparison to conventional ethanol recovery procedures.

SUMMARY OF THE INVENTION

Accordingly, one object of the present invention is to provide a technique by which substantially water free alcohol can be produced under conditions which reduce energy consumption to about 20% or less of that required by conventional methods.

Another object of the present invention is to simplify recovery methodology for substantially water free alcohol from aqueous fermentation liquors.

Still another object of the present invention is to provide a method for recovering substantially water free alcohol from aqueous fermentation liquors which utilize the low grade heat generated by the fermentation process.

Briefly, these objects and other objects of the present invention as hereinafter described will become more readily apparent can be attained in a method of producing alcohol substantially free of water by extracting an aqueous alcohol solution with an organic solvent system containing an extractant for the alcohol thereby forming a solvent-alcohol phase and an aqueous phase, and vacuum distilling the solvent-alcohol phase thereby obtaining the product alcohol substantially free of water.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

the FIGURE is a flow diagram of the alcohol extraction-distillation procedure of the invention.

DETAILED DESCRIPTION OF THE PREFERRED EMBODIMENTS

The present invention involves a method of producing alcohol which is at least substantially free of water and preferably completely free of water.

As used herein, the term alcohol embraces such common lower aliphatic alcohols as methanol, isopropyl alcohol, butyl alcohol and the like, and especially ethanol. Alcohol substantially free of water is known as absolute alcohol, which is generally 99+% alcohol.

The alcohol starting material for the method of the present invention can be prepared by any known procedure for producing alcohol. One common method of producing alcohol, especially ethanol, in appreciable quantities is fermentation, wherein a yeast microorganism is cultured for a period of time in a sugar containing medium such as molasses. Other simple aliphatic alcohols can also be produced by fermentation. The basic product of metabolism of the yeast is alcohol. Since the fermentation process is so well known, no further comment concerning fermentation is believed necessary. Exemplary methods of producing ethanol by continuous fermentation are shown in U.S. Pat. Nos. 2,371,208 and 3,591,454. Other biomass raw materials apart from sugar can also be used in fermentation, and these sources include grains such as wheat, corn, barley and the like as well as cellulosic materials. However, whenever cellulosic materials are used, they must be broken down by enzymatic action to glucose before the material can be fermented to ethanol.

In the first step of the present invention for producing alcohol substantially free of water, the aqueous alcohol solution obtained from fermentation is extracted with an organic solvent system containing an extractant for alcohol. However, before extraction the aqueous alcohol fermentation liquor should first be clarified by processing an aqueous alcohol liquor by filtration, centrifugation, or the use of a conventional beer still. In this step, it is only necessary to remove the undissolved solids which may plug conventional liquid/liquid contacting equipment. Dissolved solids need not be removed. Hence a beer still may be used, but it is not required.

For a clearer understanding of the present process, reference is made to the FIGURE which shows clarified aqueous alcohol mixture entering solvent extraction zone 3 via line 1. The solvent extraction zone 3 can be a conventional counter-current solvent extraction column. The organic solvent system enters extraction zone 3 via line 5 from vacuum distillation unit 7. The aqueous phase which forms in the extraction zone 3 is discharged as the raffinate through line 9. On the other hand, the organic solvent-alcohol phase which forms in zone 3 and which is substantially free of water is discharged from zone 3 via line 11 to vacuum distillation unit 7.

In the vacuum distillation unit 7, alcohol is separated from the components of the organic solvent system, the relative ease of which separation is determined by the solvent chosen. Preferably, a high molecular weight solvent is selected so that the vapor pressure of the solvent is much less than the vapor pressure of the dissolved alcohol. The low grade of heat produced during fermentation aids in distilling the solvent phase-alcohol mixture under vacuum conditions. Alcohol, at least substantially free of water, is discharged from unit 7 via line 13 to condensation unit 15 where the alcohol is condensed. Most of the alcohol product is withdrawn for use from the condenser through line 18, while that amount of essentially dry alcohol needed to adequately dry the organic solvent system-alcohol phase at the top of unit 3 is recycled to the unit through line 19. Normally, from one to 75 parts by wt. of the dried alcohol is recycled to unit 3 per 10 parts by wt. of the solvent-alcohol phase. Noncondensible off-gases generated in the system are discharged from the system via line 21.

A unique aspect of the apparatus of the present invention is the heat pump system shown in the FIGURE which absorbs heat present in the alcohol product vapor discharged from unit 7 to heat the alcohol-solvent phase entering distillation unit 7 through line 11. In order to provide more efficient utilization of the heat generated in the system thereby lowering energy costs, heat is absorbed from the dried alcohol product discharged through line 13 into heat exchanger 15 by a low pressure thermodynamic fluid. The hot, low pressure thermodynamic fluid is discharged from heat exchanger 15 via line 27 into compressor 26 where the vapor is compressed to a hot, high pressure vapor. The high pressure vapor discharged through line 23 into heat exchanger 20 heats the alcohol-solvent phase entering distillation unit 7. High pressure vapor, partially condensed, discharged from the heat exchanger via line 31 is sent to heat exchanger 28 where residual heat is discharged to the environment by cooling air or water entering and leaving the exchanger via line 29. The fully condensed, high pressure liquid discharged from heat exchanger 28 via line 25 is throttled across valve 22 where the liquid becomes a low pressure, cool liquid entering heat exchanger 15 via line 30. Throttle valve 22 controls the low pressure side of the thermodynamic fluid in the heat pump system.

An important aspect of the alcohol separation and recovery process of the present invention pertains to the type of material used as the organic extractant of the organic solvent system in the extraction step. The organic extractant which is used should be one which selectively complexes with alcohol and at the same time is one in which water is essentially immiscible. The solvent should also have a substantially lesser vapor pressure than that of the alcohol. Under these limitations, the relative volatility difference between the alcohol and solvent will be large. Also, the solvent performs the more difficult water/alcohol separation.

The ability of an organic extractant to efficiently separate two similar molecules such as water and alcohol depends on a delicate balance between several structural features. Factors such as hydrogen bonding capabilities, charge distribution, steric environment of coordinating centers and hydrophobic-hydrophilic balance are important considerations in recovering fuel grade alcohol efficiently. Clearly, the presence of a zwitter ionic structure in the extractant molecule (or semi polar bond) in which the negative charge in the molecule protrudes into the organic solvent medium and the positive charge is embedded in a hydrophobic environment are important structural features. This arrangement should increase the hydrogen bonding capabilities of the extractant and diminish the extent of aggregation of extractant in the hydrocarbon solvent. In order to decrease the degree of water complexation, structural features should be incorporated in the extractant that prevent the two extractant molecules from becoming proximate to one another to form a bridged structure with bridging water molecules. Secondary hydrogen bonding sites such as —O—R components should be either eliminated or sterically encumbered so as to prevent additinal interactions with water molecules. Finally, enough hydrophobic hydrocarbon framework should be incorporated into the extractant molecules to prevent any significant solubility in the aqueous alcohol phase of the extraction zone. These considerations and restrictions suggest the following type of compounds which include symmetric and asymmetric alkyl and aryl phosphates, phosphonates, phosphine oxides, sulfoxides, sulfones, amine oxides and quaternary ammonium and phosphonium salts of sterically hindered carboxylic acids possessing structural features which facilitate alcohol complexation.

Suitable examples of organic extractant compounds for use in the organic solvent system include di-2-ethylhexyl phosphate, 2-ethylhexylphosphonate, tri-neopentylphosphate, cyclohexyl di-t-butylphosphate, tri-2,6-dimethylphenylphosphate, triphenylphosphine oxide, di-neopentyl sulfoxide, di-neopentylsulfone, triisopropylamine oxide, tetra-n-butylammonium-2,6-di-t-butylbenzoate and the like. Also, the class of high-boiling alcohols such as tridecyl, dodecyl, 2-octal and the like.

In the formulation of a suitable solvent system for the extraction of alcohol from an aqueous alcohol solution, a hydrophobic solvent which is completely miscible with the organic extractant molecule should be employed. Suitable hydrophobic solvents include aliphatic hydrocarbons such as decane, dodecane and the like and hydrocarbon mixtures such as gasoline, kerosene and the like. Other suitable solvents include liquid aromatic hydrocarbons such as toluene, xylene, diisopropylbenzene and the like and halogenated hydrocarbons such as carbon tetrachloride, trichloroethylene and the like. The proportion of the organic extractant to organic solvent in the solvent system should be such that 1 part by wt. of extractant is mixed with from 0.2 to 10 parts by wt., preferably 1 to 10 parts by wt., of organic solvent. The temperature of the liquid mixture during extraction of the aqueous alcohol mixture is not critical and can vary as the temperatures of given fermentation batches vary or by the amount of heat which can be applied to the extraction step from available waste energy sources. Normally, however, the extraction step is conducted at a temperature of from 15° to 98° C. Moreover, during extraction any amount of organic solvent system which achieves the satisfactory extraction of alcohol from the aqueous alcohol mixture can be employed. Normally, however, one part by wt. of the aqueous alcohol solution is extracted with from 0.5 to 10 parts by wt., preferably 1 to 10 parts by wt., of the organic solvent system.

The organic solvent-alcohol phase discharged from the extraction zone is vacuum distilled by conventional methodology under a reduced pressure sufficient to effect distillation of the alcohol when heated by the heat pump and heat generated by the fermentation medium. Normally, a reduced pressure ranging from 1 to 500 mm Hg, preferably 1 to 450 mm Hg, is sufficient for vacuum flash stripping or vacuum flash evaporation purposes. The ethanol vapor discharged from the distillation step can be condensed by standard condenser apparatus. The alcohol product obtained from the present process is substantially free of water, normally having a water content less than 5 wt. percent.

Having generally described this invention, a further understanding can be obtained by reference to certain specific examples which are provided herein for purpose of illustration only and are not intended to be limiting unless otherwise specified.

EXAMPLE 1

The following table shows the estimated energy sinks in a conceptual fuel-grade ethanol recovery process using the method of the present invention of solvent extraction, vacuum stripping and barometric condensation of the ethanol product.

| EQUIPMENT ITEM | BRAKE HORSE-POWER | ENERGY CONSUMED (% if EtOH HV)$^a$ |
|---|---|---|
| Solvent Extraction Mixers (16 required) | 42$^b$ | 0.11$^b$ |
| Solvent circulation | 8 | 0.02 |
| Wiped Film Evaporator | 25 | 0.07 |
| Mixed Vacuum Pump | 63 | 0.17 |
| Cold Ethanol Recycle | 63 | 0.17 |
| Ammonia Refrigeration | 3120$^c$ | 8.41$^c$ |
| Cooling Water Recycle | 20 | 0.05 |
| TOTALS | 3341 | 9.00 |

$^a$Percentage of the ethanol product heating value (% of EtOH HV) when it is used as a fuel. A 33% efficiency has been assumed in producing electricity.
$^b$This is the total for the cascade.
$^c$The reference cycle evaporates at −30° F. and condenses at 120° F. to facilitate heat transfer. The energy consumed is 3.2 BHP/ton of refrigeration.

The total energy consumption appears very favorable compared to conventional distillation. This analysis suggests that the energy consumption in drying the product to 98+% ethanol may be reduced from about 61.5% to 9% of the product heating value.

Having now fully described this invention it will be apparent to one of ordinary skill in the art that many changes and modifications can be made thereto without departing from the spirit or scope of the invention as set forth herein.

What is claimed as new and desired to be secured by Letters Patent of the United States is:

1. A method for producing alcohol substantially free of water, comprising:
   extracting an aqueous alcohol solution with an organic solvent system comprising an organic solvent and an extractant for said alcohol selected from the group consisting of a symmetric or asymmetric alkyl or aryl phosphate, a phosphonate, a phosphine oxide, a sulfoxide, a sulfone, an amine oxide or a quarternary ammonium or phosphonium salt in a ratio of 1 to 10 parts by weight solvent to one part by weight extractant, thereby forming an organic solvent-alcohol phase and an aqueous phase; and
   vacuum distilling said organic solvent-alcohol phase thereby obtaining the product alcohol substantially free of water.

2. The method of claim 1, wherein said aqueous alcohol solution is obtained by fermenting a suitable biomass material and then clarifying the fermented aqueous medium.

3. The method of claim 1, wherein said extractant in said organic solvent system is a symmetric or asymmetric alkyl or aryl phosphate, phosphonate, phosphine oxide, sulfoxide, sulfone, amine oxide, quaternary ammonium or phosphonium salt or a high boiling alcohol.

4. The method of claim 3, wherein said extractant is a member selected from the group consisting of trineopentylphosphate, dibutyl butyl phosphonate, di-2-ethylhexyl phosphate, 2-ethylhexylphosphonate, cyclohexyl di-t-butylphosphate, tri-2,6-dimethylphenyl phosphate, triphenylphosphine oxide, dineopentyl sulfoxide, dineopentylsulfone, tri-isopropylamine oxide and tetra-n-butylammonium-2,6-di-t-butylbenzoate.

5. The method of claim 1, wherein, in the said extraction step, from 0.5 to 10 parts by weight of said organic solvent system are contacted with one part by weight of said aqueous alcohol solution.

6. The method of claim 1, wherein said extraction is conducted at a temperature ranging from 15° to 98° C.

7. The method of claim 1, wherein the solvent component of said organic solvent system is an aliphatic hydrocarbon, a liquid aromatic hydrocarbon, a halogenated hydrocarbon, or mixtures thereof.

8. The method of claim 7, wherein said mixed solvent is a mixture of gasoline and kerosene.

9. The method of claim 1, wherein said solvent-alcohol mixture is distilled at a reduced pressure ranging from 1 to 500 mm Hg.

10. The method of claim 1, which further comprises:
    condensing the alcohol vapors obtained by vacuum distilling said solvent-alcohol phase in a heat exchange device; and
    recycling a portion of said condensed alcohol substantially free of water to said extraction step to enhance the drying of alcohol in said solvent-alcohol phase.

11. The method of claim 10, wherein from 1 to 75 parts by wt. alcohol are recycled per 10 part by wt. of solvent-alcohol phase.

12. The method of claim 10, wherein heat in said alcohol product substantially free of water is recycled in the process by:
    (a) absorbing heat in said heat exchange device by a low pressure thermodynamic liquid;
    (b) compressing the low pressure vapor obtained to a high pressure vapor; and
    (c) transferring the heat in said compressed vapor to said organic solvent-alcohol phase being vacuum distilled.

13. A method for producing alcohol substantially free of water, comprising:
    extracting an aqueous alcohol solution with an organic solvent system comprising an organic solvent and an extractant for said alcohol selected from the group consisting of a symmetric or asymmetric alkyl or aryl phosphate, a phosphonate, a phosphine oxide, a sulfoxide, a sulfone, an amine oxide or a quarternary ammonium or phosphonium salt in a ratio of 1 to 10 parts by weight solvent to one part by weight extractant, thereby forming an organic solvent-alcohol phase and an aqueous phase;

heating said organic solvent-alcohol phase;

vacuum distilling said heated organic solvent-alcohol phase thereby obtaining a substantially water free alcohol vapor;

condensing and withdrawing heat from said alcohol vapor by a low pressure thermodynamic fluid; and transferring the heat in said low pressure thermodynamic fluid to the organic solvent-alcohol phase being sent to said vacuum distillation unit by means of a heat pump.

* * * * *